(12) United States Patent
Lykke (10) Patent No.: US 8,318,079 B2
(45) Date of Patent: Nov. 27, 2012

(54) HYDRACTIVE RECIPE

(75) Inventor: Mads Lykke, Broenshoej (DK)

(73) Assignee: Coloplast A/S, Humlebaek (DK)

( * ) Notice: Subject to any disclaimer, the term of this patent is extended or adjusted under 35 U.S.C. 154(b) by 501 days.

(21) Appl. No.: 12/086,038

(22) PCT Filed: Dec. 19, 2006

(86) PCT No.: PCT/DK2006/000726
§ 371 (c)(1),
(2), (4) Date: Jun. 17, 2008

(87) PCT Pub. No.: WO2007/071246
PCT Pub. Date: Jun. 28, 2007

(65) Prior Publication Data
US 2009/0311307 A1    Dec. 17, 2009

(30) Foreign Application Priority Data

Dec. 23, 2005    (DK) ................................. 2005 01831

(51) Int. Cl.
*B05D 3/12*    (2006.01)

(52) U.S. Cl. ........ 264/643; 264/482; 264/153; 264/154; 264/155; 264/156; 264/642; 264/265; 264/504; 264/273; 264/279

(58) Field of Classification Search .................. 264/134, 264/136, 482, 153, 155, 156, 642, 643, 265, 264/504, 135, 273, 279, 154
See application file for complete search history.

(56) References Cited

U.S. PATENT DOCUMENTS

| 4,231,369 | A | | 11/1980 | Sorensen et al. |
| 4,367,732 | A | | 1/1983 | Poulsen et al. |
| 4,539,256 | A | * | 9/1985 | Shipman .......................... 264/41 |
| 4,613,544 | A | | 9/1986 | Burleigh |
| 4,616,644 | A | | 10/1986 | Saferstein et al. |
| 4,867,748 | A | | 9/1989 | Samuelsen |
| 5,051,259 | A | | 9/1991 | Olsen et al. |
| 5,336,554 | A | * | 8/1994 | Knight .......................... 428/137 |
| 5,714,225 | A | | 2/1998 | Hansen et al. |
| 5,968,855 | A | * | 10/1999 | Perdelwitz et al. ........... 442/341 |
| 6,171,594 | B1 | | 1/2001 | Nielsen |
| 6,300,413 | B1 | | 10/2001 | Simon et al. |
| 6,303,700 | B1 | | 10/2001 | Chen |
| 6,437,038 | B1 | | 8/2002 | Chen |
| 6,451,883 | B1 | | 9/2002 | Chen et al. |
| 2005/0271712 | A1 | * | 12/2005 | Shannon ....................... 424/445 |

FOREIGN PATENT DOCUMENTS

EP     1679085 A2 *  7/2006
WO    WO 89/05619    6/1989
(Continued)

*Primary Examiner* — Joseph Del Sole
*Assistant Examiner* — Timothy Kennedy
(74) *Attorney, Agent, or Firm* — Jacobson Holman PLLC (57) ABSTRACT

The invention relates to a method for assembling an adhesive device comprising a first matrix-forming material with holes and a second material, the method comprising:
(a) compose the first matrix-forming material with holes;
(b) compose the second material with a Tm lower than the Tm of the first material, while enabling increase in the Tm of the second material;
(c) assemble the adhesive device by filling the holes of the first matrix-forming material of step (a) with the deformable second material of step (b) at a temperature where the second material is deformable and the first material is non-deformable;
(d) increase the Tm of the second material.

19 Claims, 4 Drawing Sheets

FOREIGN PATENT DOCUMENTS

| | | |
|---|---|---|
| WO | WO 94/15562 | 7/1994 |
| WO | WO 00/54820 | 9/2000 |
| WO | WO 01/05340 A2 | 1/2001 |
| WO | WO 02/066087 A1 | 8/2002 |

* cited by examiner

HYDRACTIVE RECIPE

This is a national stage of PCT/DK2006/000726 filed Dec. 19, 2006 and published in English.

FIELD OF THE INVENTION

The present invention relates to a method for assembling an adhesive device comprising a first matrix-forming material with holes in it, and a second material to be filled into the holes. This is industrial scale hole-filling.

BACKGROUND

A variety of adhesive devices are known which consist of or comprise a skin-friendly adhesive material which may e.g. comprise a continuous phase containing the adhesive. In these products there is often a discontinuous phase, which comprises e.g. one or more water-soluble or water-swellable hydrocolloids, starch derivatives or cellulose derivatives or hydrophilic polymers, and optionally one or more medicaments.

WO 89/05619 describes a skin plate product consisting of a matrix material and a plurality of alternating zones of a different material where at least one material is a self adhesive. In this product the zones of the second material extend through the entire thickness of the product and the zones are parallel and extend in a direction usually at right angles to the main surfaces of the product. Such a product may be produced by laminating and rolling plates or sheets of the two materials and then cutting the rolled product perpendicularly to the axis thereof.

WO 94/15562 describes a skin plate product consisting essentially of the same materials as described in WO 89/05619. According to WO 94/15562 the skin plate product comprises at least two material units being of different materials, at least one of which is a skin-friendly self-adhesive material and where a first material unit extends through the area of the entire product forming a matrix, this material unit further constituting at least a portion of the first surface and the second surface, respectively and the additional material unit or units constituting the other portion of the first and the second surface, respectively. Typically, the additional unit comprises a material which is different from the matrix material and extends somewhat into the product but not entirely through the product and the product therefore has different properties on opposite sides. These products are produced when pressing the second material into the matrix material.

U.S. Pat. No. 4,231,369 and U.S. Pat. No. 4,367,732 disclose ostomy systems or skin barriers having different elements including a gel-like adhesive material consisting roughly of a continuous phase of Physically X-linked elastomer (styrene-olefin-styrene block-copolymer), a hydrocarbon tackifier, a plasticiser (optional), and an oil (optional); and a discontinuous phase of hydrocolloid dispersed in the continuous phase. In the disclosed type of adhesives the discontinuous phase is simply mixed into the continuous phase.

SUMMARY

The present invention relies on the finding that controlling the melting point (Tm) of a hole-filling material of an adhesive device such that it during manufacturing is a somewhat fluid substance at a temperature where the matrix of the adhesive device is somewhat stiff, allows the hole-filling material to flow into the matrix. After the assembly, the melting point of the hole-filling material is raised to obtain a somewhat solid and coherent adhesive device.

DETAILED DISCLOSURE

Thus, one aspect of the present invention relates to a method for assembling an adhesive device comprising a first matrix-forming material with holes and a second material, the method comprising:
(a) compose the first matrix-forming material with holes;
(b) compose the second material with a Tm lower than the first material, while enabling increase in the Tm of the second material;
(c) assemble the adhesive device by filling the holes of the first matrix-forming material of step (a) with the deformable second material of step (b) at a temperature where the second material is deformable and the first material is non-deformable;
(d) increase the Tm of the second material.

What is obtained is that a second (hole) material can be fixed into preformed holes of the first (matrix) material by means of a physical or chemical process. The adhesive device with holes is assembled, when the second material is put Into the holes.

The adhesive device of the present invention is preferably a flat skin plate product for use as a semi-manufacture in the production of dressings, skin- and wound-care devices, fastening means for dressings, ostomy equipment, breast prostheses, wound drains and catheters for incontinence equipment, in particular for men, and for use in electrodes for application to the skin.

The product according to the invention may be circular, oval, square or rectangular or have any other embodiment. For use in ostomy equipment the product produced according to the invention may e.g. have a central aperture.

In a further aspect, the invention relates to an ostomy appliance comprising an adhesive device of the invention as a part of or all of an adhesive wafer for adhering such ostomy appliance to the skin. Such ostomy appliances may, apart from the skin plate product, of the invention be of a kind known per se and may be made in analogy with products in the art. Such ostomy appliances may be one-piece appliances or a body side member which together with an exchangeable collecting member forms a conventional two-piece appliance.

In a still further aspect the invention relates to a wound dressing comprising an adhesive device of the invention as a part of or all of an adhesive surface for adhering such wound dressing to the skin.

According to the present invention the adhesive device or part of the adhesive device is prepared by the method of the invention.

The matrix-forming material is preferably selected from the group consisting of styrene-isoprene-styrene block copolymers, polyisbutylenes, polyvinylether or polyacrylates, polyemethacrylates, or copolymers thereof, and silicone.

The invention solves the problem of filling holes in a thermoplastic, or thermo-sensitive matrix material. The problem is, that if the temperature of the second material is increased, to decrease viscosity, the matrix material will melt or become damaged.

In a preferred embodiment, the matrix-forming material is thermoplastic. However, the problem is also present for non-thermoplastic materials. For example materials containing hydrocolloids, or containing active substances, such matters will decompose or be damaged when exposed to elevated temperatures. Thus, in one embodiment, the matrix material contains temperature sensitive substances, such as hydrocolloids or active substances.

The skin-friendly adhesive may be of any kind, e.g. an acrylic adhesive, a hydrogel adhesive or a hydrocolloid adhesive. The adhesive material may e.g. comprise caoutchouc, caoutchouc-like synthetic homo-, co- or block-copolymers, polyacrylate and copolymerisates thereof, polyurethane, silicone, PPO, Akrylat blockcopolymer polyisobutylene, polyvinyl ether and natural or synthetic resins or mixtures thereof optionally containing zinc oxide. The adhesive matrix may further contain various additives, such as plasticisers, thickeners and others, and optionally various medicaments, such as antiseptics, hormones, nicotine etc.

Skin-friendly adhesive may suitably be a medical grade barrier adhesive known in the art such as the formulation being disclosed, for example in U.S. Pat. Nos. 4,367,732, 5,051,259, 5,714,225, 6,171,594, 6,303,700, 6,451,883 or 6,437,038, or in WO Applications Nos. 00/54820, or 01/05340.

In a preferred embodiment the first matrix-forming material is a soft, hydrophobic adhesive, which is very skin-friendly and has a very high resistance towards erosion by water. Examples of such materials are SIS/SI gels, Silicone gels, PPO gels, Acrylic block copolymer gels, and PU gels. The second material is then chosen according to its purpose such as absorption of water, release of a biologically active substance or other. According to the invention a large freedom in the pattern of the holes in the matrix-forming material is provided. Hence, there are not necessarily special requirements to the adhesive properties or the erosion resistance of the second material.

Adhesive surfaces are preferably protected by a protective cover or a releasable liner until use. A protective cover or releasable liner may for instance be siliconized paper. It does not need to have the same contour as the product, e.g. a number of products may be attached to a larger sheet of protective cover. The protective cover is usually not present during the use of the product of the invention. Furthermore, the edge of the product may be beveled as disclosed in U.S. Pat. No. 4,867,748.

Often the term "hole" as described in the invention relates to depressions extending somewhat into the matrix material or passages extending from one side of the product to the other side of the product. Thus, the hole or the zone comprising the second material, will typically extend from one surface of the adhesive to the other, despite that the hole might not be filled completely.

Holes are preferably made without turning or tilting the first matrix-forming adhesive during the process. Hence, holes with slanting angles are preferably made using laser technology but can be made using other technologies although with higher process complexity.

According to the method of the invention holes formed in the first matrix-forming material are alternatively made by mechanical means e.g. by using punching machines, drills or pins. However, it is preferred to use a contact free method such as radiation-, hot air-, or water jet technology.

Especially preferred is the use of laser technology for materials removal. Lasers of a wide variety can be used including continuous and pulsed $CO_2$—, diode-, Nd:YAG- and Excimer lasers. Lasers are relatively inexpensive, easily integrated into production lines and allow for a very quick and inexpensive change from one pattern to another simply by changing the programming. Very complex patterns with high precision and fine details can be made using a laser with very little extra effort and without making the production considerably more expensive. Furthermore, lasers provide an easy control of the shape and depth of holes, allow holes to be made on both surfaces of the product and can provide secondary structures on a skin plate product after forming a primary structure, e.g. the holes.

Many of these advantages are, to a certain extent, also obtained using other contact free technologies.

In a series of embodiments of the invention, it is preferred that the zones comprising the second material, that is, the holes filled with the second material, extends from the top to the bottom surface of the adhesive, and wherein the exposed area of the second material at the top surface of the adhesive describes a different pattern than the exposed area of the second material at the bottom surface of the adhesive.

By different pattern is generally meant that they look different. In one embodiment the exposed area of the zone comprising the second material at the top surface of the adhesive is larger than the exposed area of the zone comprising the second material at the bottom surface of the adhesive.

In one embodiment the distribution of the exposed area of the zone comprising the second material at the top surface of the adhesive is different from the distribution of the exposed area of the zone comprising the second material at the bottom surface of the material.

In one embodiment the density of the exposed area of the zone comprising the second material at the top surface of the adhesive is different from the density of the exposed area of the zone comprising the second material at the bottom surface of the material.

In one embodiment the areas of at least two neighboring holes at one of the surfaces are sufficiently large to be interconnected.

Such products provide a freedom for tailoring a skin plate product with respect to controlling the properties and the distribution thereof over the first and second surfaces of the product, which is not possible for products of the state of the art. Especially, it is easy to provide products wherein the areas of the first and second surfaces are of different size, of different distribution and/or of a different pattern.

The zones comprising the second material, that is the holes in the skin plate product according to the invention comprising the second material, can have varying shapes and forms. In one embodiment, the areas of the first and second surfaces are of different size on the surfaces of the skin plate product. Moreover, the area of the zones comprising the second material on the first surface (the top surface) and the area on the second surface are preferably of any arbitrary shape such as irregular or regular shape such as in the shape of a rectangle, square, triangle, star, parallelogram, rhomb, ellipse, circle, super-ellipse or super-circle.

According to a preferred embodiment of the invention at least one of the holes does not intersect at least one of the surfaces. In this way different areas are obtained on one surface of the skin plate product compared to the other surface of the skin plate product.

In an another embodiment the second material is in the form of cylindrical bodies having their axes essentially perpendicular to the planes of the first and second surfaces and at least one of the cylinders has a length shorter than the thickness of the skin plate product. This is an alternative way to provide different areas of the zone on one surface of the skin plate product compared to the other surface of the skin plate product.

According to a preferred embodiment of the invention, the second material is in the form of bodies of frustum of cones. This is an alternative way to provide a product with different areas on one surface of the skin plate product compared to the other surface of the skin plate product. The cones can be arranged in any fashion e.g. where the basis of the cones is positioned alternating on the first and the second surface of the skin plate product or e.g. where a majority of the cones have their basis on one side of the product. It is also possible that all the cones have their basis at the same surface. In these embodiments the areas of the cone shaped holes in the first and the second surface are not only different but furthermore some of the cones may only be present on one side of the product. Hence, different properties are obtained on the first and the second surface of the product.

Furthermore, using slanting angles, the boundary surface between the holes and the first matrix-forming material can vary, giving the holes an irregular shape.

According to yet another preferred embodiment of the invention, the second material is in the form of cylindrical bodies having slanting axes in relation to the planes of the first and second surfaces and at least one of the cylindrical bodies has a length insufficient to reach from one surface of the product to the other surface.

The axes of the slanting cylindrical bodies can be arranged in a parallel or non-parallel fashion.

According to another preferred embodiment of the invention, the boundary surface between holes and the first matrix-forming material is in the form of a surface which intersects the first and second surfaces in slanting angles (referred to as the angle alpha in the figures). Hence, the areas of the first and second surfaces constituted by the second material can have arbitrary shapes which are differently distributed.

When the second material is in the form of cylindrical bodies having slanting axes in relation to the plane of the first and the second surfaces, the areas of the holes on the surfaces are at different locations on each side of the product. Therefore, it is possible to e.g. focus the properties of the materials in the holes on a specific location on one side of the skin plate product, but maintaining an even distribution of the holes on the other side of the product. This will result in the possibility of controlling the properties of the skin plate product optimally.

It is also foreseen that the holes may have at least a symmetrical plane to at least one of the first or second surfaces. Another option is that there is a symmetrical axis through the centre of the area of the first or second surface constituted by the second material and the holes will obtain the shape of e.g. a cylinder, pyramid or a cone.

Furthermore, in another embodiment of a skin plate product according to the invention it is possible that all of the holes for taking up a second material extend through the entire thickness of the product. In this embodiment of a skin plate product the slanting angle of the boundary surface between the second material and the first matrix-forming material can vary as described above. Accordingly, the holes may have an irregular shape.

When the holes have a conical or a pyramidal shape the materials in the holes can have a bigger effect on one side of the skin plate product compared to the other side of the product as the holes cover a different sized area on the surfaces. This could for example be used to control the peeling force of the skin plate products from the skin, and also to provide different peeling force in different directions for reducing the risk of unintended removal of the product during use and facilitating in tended removal of the product.

According to yet another preferred embodiment of the invention, the areas of at least two neighbouring holes at one of the surfaces are sufficiently large to be interconnected.

In this case the interconnected part of the holes can form a unit of a second material which can be made out of a material which has large absorbing capacity. In a skin plate product where the first matrix-forming material is made out of skin-friendly adhesive, it is possible to obtain a skin plate product where one side of the product has good adhesive properties and also provides a high capacity of transporting large amounts of fluid from the skin surface. In this type of a skin plate product, such units may serve as a reservoir and may even be exchanged with another unit of the same material without requiring that the skin plate product be removed.

A skin plate product where some of the holes are interconnected essentially forming a pad on one side of the product can be advantageous in highly exudative wounds. The many holes on one side of the product will then function as multiple channels that draw liquid from the wound to the pad on the other side of the product which is capable of containing a large amount of liquid. This pad can optionally be replaced with another similar pad when the first pad is saturated. Thereby, the whole dressing on the wound does not need to be replaced.

In general, the same material can be used for the second material as used for the matrix-forming material. Thus, in a preferred embodiment, the second material is thermoplastic.

In one embodiment, the second material contains hydrocolloids. The hydrocolloids contained in the second material are suitably water soluble or water swellable hydrocolloids. Such hydrocolloids are naturally occurring hydrocolloids such as guar gum, locust bean gum, pectin, alginates, gelatine, xanthan or karaya gum, semisynthetic hydrocolloids such as cellulose derivatives, e.g. salts of carboxymethylcellulose, methylcellulose and hydroxypropylmethylcellulose, sodium starch glycollate and synthetic hydrocolloids such as polyvinyl pyrrolidone, polyvinyl alcohol, polyethylene glycol or certain polyacrylates. In a special embodiment, the hydrocolloid particles are microcolloids such as described in WO 02/066087.

It is preferred that the matrix-forming material or the second material, but most preferably both materials are skin friendly adhesives. When determining whether adhesives are "skin-friendly", it is usually based on passing tests of Cytotoxicity, Primary Skin Irritation and Sensitization. Also, preferably, a skin friendly adhesive has a melting point above 50° C.

In one aspect of the invention a plasticiser is added to the second material whereby the Tm of the second material is lowered. The examples illustrate the use of DOA and TXIB from Eastman as a plasticising materials that will migrate into the SIS based matrix-forming material. As the plasticiser migrates, the Tm of the second material is increased. That is, the effect as a melting point lowering substance is deactivated.

In general, the plasticiser used in the second material shall be small (that is small Mw) and be soluble in the matrix material.

As this SIS matrix in general is predominantly a non-polar matrix, more polar components will not, or only sparingly, migrate into the matrix. Consequently, when using more polar matrices, such as silicone- or acryl-based matrix-forming materials, the use of a somewhat more polar plasticisers such as Citrofol BII is recommended.

In another aspect of the invention, a solvent is added to the second material. This will decrease Tm. One example of a solvent is toluene (see example 7). This will make the second material sufficiently formable to fill the holes and the solvent will subsequently evaporate, whereby the effect as melting point lowering substance is deactivated and thereby leaving the second material with a higher melting point.

In a similar embodiment the second material is inhibited from hardening due to the presence of a solvent. An example of such system is acidic acid hardening silicone as the second material.

In another embodiment of the invention, the second material has low viscosity, but can be hardened using e.g. by UV polymerisation or heat after being filled into the holes.

The need for lowering the melting point of the second material arises from the need to fill the holes in the matrix-forming material. To satisfy this, the second material must be softer and more deformable than the matrix-forming material. However, the heat transmission in the matrix-forming material is typically very low, and if that matrix-forming material is provided cold (relative to the melting temperature of the matrix-forming material) the difference in Tm (melting temperature) between the substances do not need to be more than e.g. 10° C., without melting the matrix-forming material. In a preferred embodiment the differences in Tm might be more than 10° C., such that more than 15° C., or more than 20° C., or more than 25° C. or even more than 30° C.

In a preferred embodiment, the $T_m$ of the second material is 10° C. higher than the $T_m$ of the matrix forming material.

The idea behind the increase in Tm (e.g. by deactivation) is to obtain a change in the physical properties of the second material. That is, it is transformed from a soft, formable material to a cohesive substance.

In one aspect, the increase in Tm of the second material is performed by evaporation.

In another aspect, the increase in Tm of the second material is performed by migration of a melting point lowering substance, typically into the matrix-forming material. By using the migration deactivation procedure the melting point lowering substance will not create waste—that will need special attention and thereby increase production cost. Also, to account for the added plasticiser in the matrix-forming material, this material is provided with less plasticiser than should be in the final product. As a result, the matrix-forming material is harder (has an even higher Tm) during assembly, which further eases the assembly and increases the difference in Tm.

In yet another aspect of the method of the invention, the increase in Tm of the second material is obtained by inducing reaction between two components of a reactive polymer system in the second material. An example thereof is polymerisation by light preferably controlled with an activator. Another example is polymerisation controlled by a cross-linker.

A particular preferred embodiment uses a combination of some of the above techniques. Here, the second material comprises component B of a two component reactive system. This two component reactive system will polymerise when present together typically aided by heat or light. Component A of the two component reactive system is placed in the matrix material, but this component A is of low molecular weight and is highly soluble in the second material. Thus, when the second material is placed in the holes of the first material, component A will migrate from the matrix material into the second material, and the polymerisation can be initialised. This system provides freedom in the product process. Despite that the polymerisation of a two component system is aided by heat or light, a spontaneous polymerisation takes place. This spontaneous polymerisation limits the storage time of the second component. By keeping components A and B separate until polymerisation is appropriate, that is when the holes of the matrix material are filled with the second material, the storage time of the second material is increased. A similar effect is obtained if the reactive components A and B are placed in the hole material and a needed catalyst is placed in the matrix, where the catalyst migrates to the hole material and catalyses a reaction that increases Tm of the hole material.

When selecting the component to migrate from the matrix to the dot-material (the second material), the component should be, at least weakly, dissolvable in the matrix material, should not react with the matrix adhesive and should be stable during the processing of the matrix material. An example of such system is a matrix material of STRATA (pMMA-pBA-pMMA), mixed with the SPOX catalyst. The second material in this example is SPOX components A and B along with hydrocolloids, i.e. Vinylterminated PPO+crossbinder+hydrocolloids.

EXAMPLES

Example 1

Hydrophobic Adhesives

The overall aim in the design of the adhesive matrix is an adhesive with minimal skin damage, and hence also for an adhesive with minimal mechanical skin damage. We used Gel-like (tenacious) hydrophobic adhesives of the thermoplastic, SIS based type with silicone like moduli.

TABLE 1

Compositions of matrix materials in % of the constituents.

| | Matrix I | Matrix II | Matrix III | Matrix IV |
|---|---|---|---|---|
| Quintac 3520 | 30 | | | 30 |
| PL500 | 33.5 | | 36.2 | 33.5 |
| Arkon P90 | 24.5 | | 23.2 | 33.5 |
| Oppanol B50 | 10.0 | | 17.3 | |
| Citrofol BII | 2.0 | | | 3 |
| Kristalex F85 | | 30 | | |
| LA2140 | | 34 | | |
| LA1114 | | 36 | | |
| Kraton D1119 | | | 23.2 | | where:
Quintac 3520 is a SIS/SI polymer from Nippon Zeon
PL 500 is a white mineral oil
Arkon P90 is a C5 resin from Arakawa Chemicals
Oppanol B50 is PIB from BASF
Citrofol BII is a plasticiser (acetyltributyl citrate) from Jungbonzlaver
Kristalex F85 is a hydrogenated rosin resin from Eastman Chemical Company
LA2140 is a PMMA-PnBA-PMMA triblock from Kuraray Co. Ltd
LA1114 is a PMMA-PnBA diblock from Kuraray Co. Ltd
Kraton D1119: SIS/SI polymer from Kraton Polymers.

Example 2

Laser Drilled Holes

Holes are drilled in 0.3 to 1 mm thick adhesive sheets using a conventional continuous power $CO_2$ laser equipped with galvanometric-scanner mirrors and a f=300 mm meniscus lens (Allprint Smart 50 from Alltec). Movement of the laser beam is controlled using the ALLPRINT Smart Job software, the shape of drilled features is controlled by adjusting the laser marking parameters given in the table below to suit the material of choice. Most laser-marking software provide similar features to those listed in the table.

| Laser marking parameter | value |
| --- | --- |
| Power | The laser power |
| Mark velocity | Velocity of laser spot with the laser turned on |
| Jump velocity | Velocity of laser spot with the laser turned off |
| Jump delay | Break time after each jump |
| Mark delay | Break time at the end of each laser stroke |
| On delay | The time between starting of the galvo mirrors at the beginning of the stroke and turn-on of the laser beam |
| Off delay | The time between stopping of the galvo mirrors at the end of the stroke and turn-off of the laser beam |

Laser marking parameters used to control the shape of drilled features. The parameters must be optimised to each individual material.

Example 3

Hole Materials

Examples of hole-materials (second materials):

TABLE 2

Composition of dot-materials in % of the constituents

|  | Dot I | Dot II | Dot III | Dot IV | Dot V |
| --- | --- | --- | --- | --- | --- |
| Kraton D1161 | 25.0 | 25.0 | 25.0 | 25.0 | 11.8 |
| MC1 | 50.0 | 50.0 | 50.0 | 50.0 | 23.6 |
| DOA | 25.0 |  |  |  |  |
| TXIB |  | 25.0 |  |  | 17.5 |
| Citrofol BII |  |  | 25.0 |  |  |
| PL500 |  |  |  | 25.0 | 47.5 | where
Kraton D1161 is a SIS/SI polymer from Kraton Polymers
MC1 is a 40% dispersion of MicroColloids (DP209-93114) from Ciba Specialty Chemicals
DOA is Di oxhyl adipat from Cognis Performance Chemicals
TXIB is a plasticiser from Eastman Chemicals
Citrofol BII is a plasticiser (acetyltributyl citrate) from Jungbonzlaver
PL 500 is a white mineral oil.

The hole materials was prepared as described in WO02/066087.

The best dot material developed to date is material (Dot II) due to these parameters:

| Parameter | value |
| --- | --- |
| Absorption capacity | High |
| Absorption speed | High |
| Melt viscosity | Medium |
| Wet cohesion | Good |
| Procesability | Good |

Kraton D1161 was selected to provide good cohesion and good moisture kinetics. TXIB was selected due to its good plasticising properties combined with low Tg and high migration speed.

Example 4

Hydrophilic Dots

Second Material

Migration

The primary function of the hydrophilic dots is moisture handling.

A requirement is that the dot material can be processed and combined with the hydrophobic material. This example are based on a laser hole drilling process in the matrix-forming material. Consequently, the aim is to identify a fairly liquid dot material, which is made cohesive after being put into the holes.

The present example uses plasticised MC1 (microcolloids)/SIS to obtain low viscosity. The MC1/SIS material is formulated in a way, which renders it suitably low viscous at temperatures below the melting temperature of the hydrophobic matrix material to allow processing without destroying the carefully drilled holes. The plasticiser is chosen so that it will migrate into the bulk of the hydrophobic material plasticising that slightly and in the same process hardening/fixating the dots.

A series of such materials has been formulated (see examples 1 and 3). Then, app. 1 mm sheets of Matrix I and Matrix II were thermoformed by warm pressing the adhesive between two release liners. 1.5 mm holes were drilled in four Matrix I sheets, the area coverage being about 20%.

The four dot materials were heated to a melt temperature of about 100° C.

Dot material Dot IV did not melt sufficiently to produce a workable mass and was discharged. This underlines that mineral oil does not reduce the melting point of SIS/SI very much.

Dot material I, II and III all produced nice workable masses and they were applied as an about 300-500 micron layer on top of the adhesive plates. The adhesive was evaluated when applied (day 0) and after 5 days of storage at 40° C. (day 5). Plastic being a honey-like, high viscous, sticky substance; elastic gel being a soft cohesive, non-sticky mass.

|  | Matrix I (SIS/SI) 0 days/5 days, 40 C. | Matrix II (pMMA-pBA-pMMA) 0 days/5 days, 40 C. |
| --- | --- | --- |
| Dot I (DOA) | Plastic/Elastic gel | Plastic/Elastic gel |
| Dot II (TXIB) | Plastic/Elastic gel | Plastic/Elastic gel |
| Dot III (Citrofol BII) | Plastic/Plastic | Plastic/Elastic gel |
| Dot IV (PL500) | N.A./N.A. | N.A./N.A. |

As can be seen, DOA and TXIB based DOT material work well in both SIS/SI and pMMA-pBA-pMMA adhesives. This is because they have good solubility in both materials. It was surprisingly found that Citrofol BII plasticised dot material were not able to harden in SIS/SI matrix. It is speculated that it is because Citrofol BII do not migrate significantly in the chosen matrix material, due to low solubility. Citrofol BII, on the other hand, worked well in the slightly more polar acrylate block co-polymer (Matrix II). DOA formulations proved to be fairly easy to fixate as DOA apparently quickly migrates into this matrix. The same results were obtained with TXIB from Eastman.

Example 5

Design of Layered Hole Materials

Conical holes is drilled in 1 mm thick adhesive sheets made by thermoforming Matrix IV between two PE liners as described in example 2. The holes are filled with hole material Dot V as described above (example 3)

Figure 1:
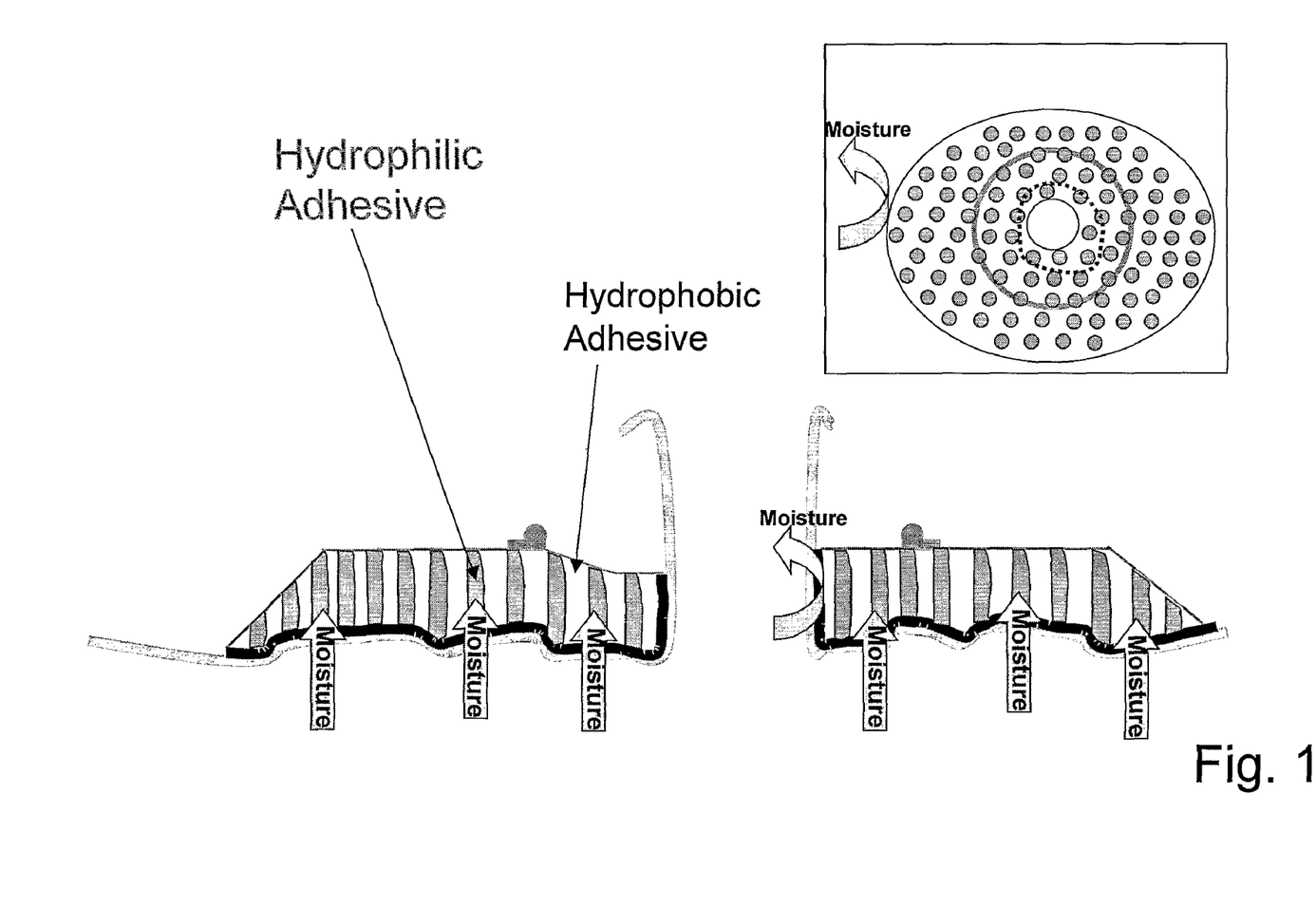
Figure 2:
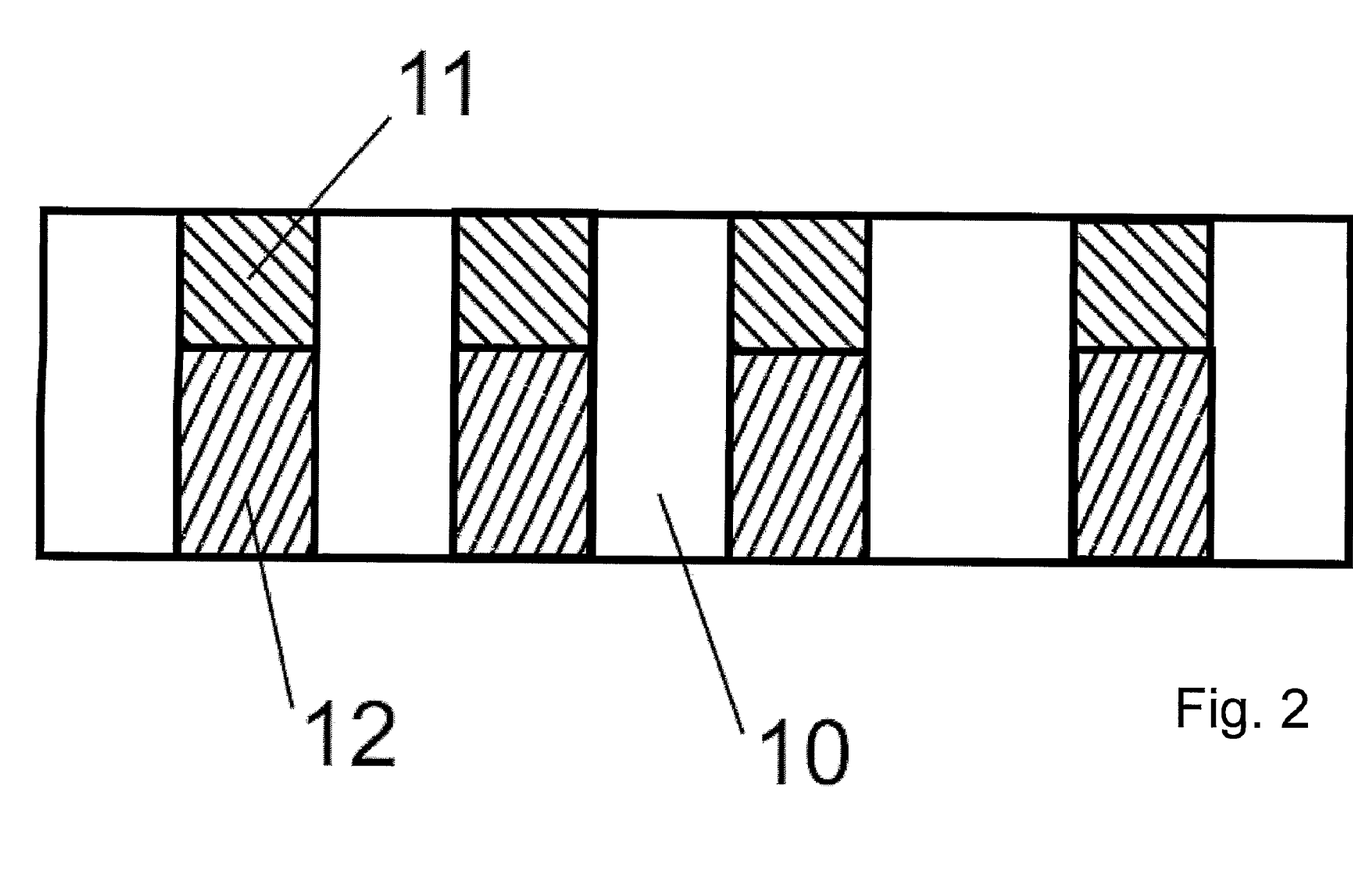

Hole material Dot V has a low concentration of polymer compared to the Matrix IV material. This implies that a substantial amount of oil and plasticiser will migrate into the matrix and reduce the volume of hole material, i.e. the materials in the holes shrink. In this case shrinkage of up to 50% of the hole material is observed after two weeks of storage. This is an example of how to make an adhesive construction with not-completely filled holes as shown in FIG. 2.

Figure 3:
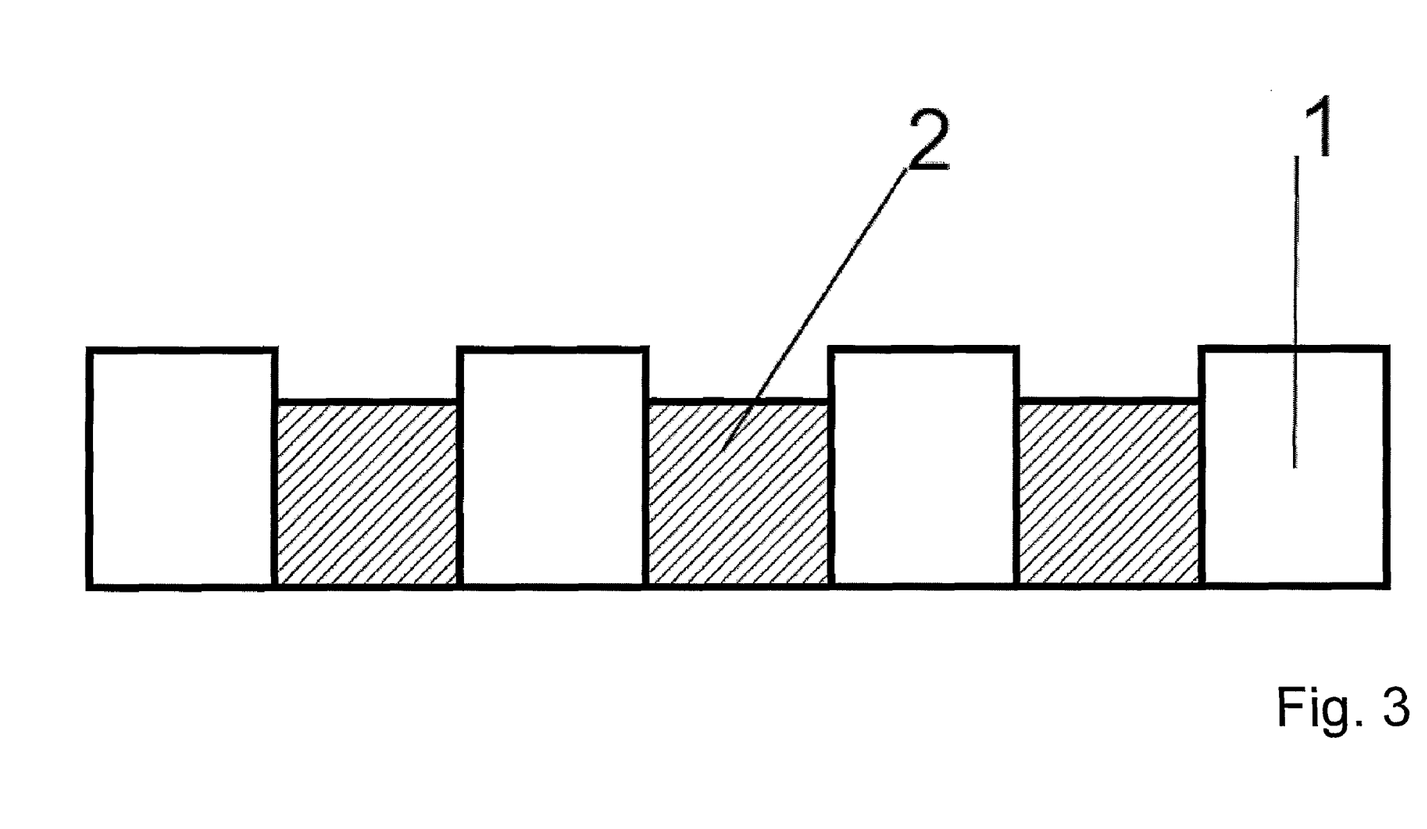
Figure 4:
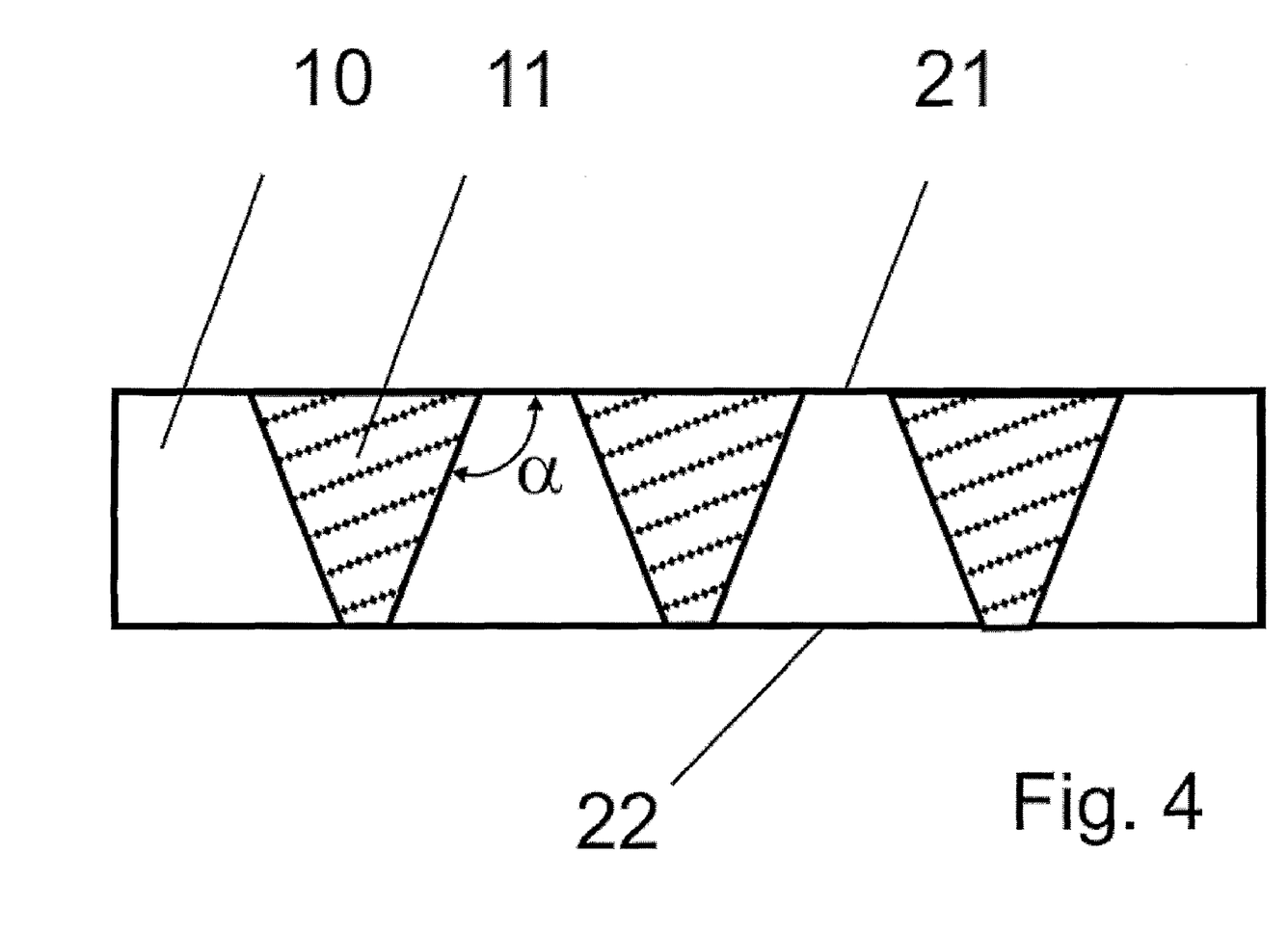
FIG. 4 shows a cross-sectional view of a skin plate product with a matrix-forming material (10) intersected by a plurality of holes (11). Zones (11) cover different areas on faces (21) and (22) but extend though the entire thickness of material (10); thus, total area of the holes on the top surface (21) is larger than the total area of the holes on the bottom surface (22). The angle between the top surface and the slanting angles of the zone of the second material is referred to as alpha ($\alpha$).

An adhesive construction as shown in FIG. 3 is made by refilling of the holes with e.g. hole material Dot II after two weeks storage of the adhesive with partially filled holes.

Example 6

Reactive Deactivation

Dot material recipes:

|  | Dot VI | Dot VII | Dot VIII | IX |
|---|---|---|---|---|
| PPO ACS220 | 78.7 | 59.1 | 68.9 | 49.0 |
| Crosslinker, CR500 | 1.2 | 0.9 | 1.0 | 1 |
| Catalyst | 0.1 | 0.1 | 0.1 | 0.0425 |
| Aquasorb A500 | 20.0 | 40.0 |  |  |
| Aquasorb A800 |  |  |  | 25 |
| Blanose |  |  |  | 25 |
| SAP |  |  | 30.0 |  |

Materials: Vinyle functionalised PPO, ACS220(Kaneka), Silanyle x-linker CR500 (Kaneka), Platinum catalyst (Kaneka).

Matrix material Matrix III (see example 1) was used.

A suitable hydrophilic dot material is produced by applying a 2 component reactive polymer system. Examples of such 2 component reactive polymer systems in hydrophilic dot material are Dot VI, VII, VIII and IX. The procedure was:

A) Adhesive plates with holes were prepared as described in example 5 (Matrix III matrix, 1.5 mm holes, app. 20% coverage)
B) The polymer, cross linker and catalyst were mixed to produce a syrup like mixture.
C) The hydrocolloids was mixed into B producing a honey like mass.
D) The hydrophilic mass from C was filled into the holes of A manually, and excess C was removed using a suitable blade.
E) The perforated release liners was replaced on one side by a breathable PU film and with a fresh non perforated release liner on the other.
F) The dot material was cured 20 min at 100° C. in an oven.

The resulting adhesives were nice and uniform and seem to adhere well to skin.

Example 7

Evaporation Deactivation

Using the material Dot II (Example 3) without TXIB, a 50% solution of dot material may be produced by:

A) Preparing a 25% Kraton D1161 solution in Toluene by mixing 1 part Kraton granules with 3 parts solvent at room temperature.
B) Mixing 2 parts Kraton solution (A) with 1 part MC1 to produce a 50% solution of dot material with the composition:
   1 part Kraton D1161
   2 parts MC1
   3 parts Toluene
C) Matrix adhesive with holes may be produced as in Example 2. One of the release liners with holes is replaced by a film or a non perforated release liner to avoid the relative low viscous solution B to leak through the holes.
D) The holes in C is filled with solution B. Any excess can be scraped off with a suitable blade.
E) The filled adhesive from D is then left in a well ventilated area and the Toluene is allowed to evaporate. The evaporation process may be speeded up by heat.

The result is an adhesive according to the invention.

FIGURES

FIG. 1

This figure shows a schematic diagram of the construction of the adhesive plate according to the invention. As moisture is absorbed through holes perpendicular to the plane of the plate, no horizontal spreading of absorbed material will take place.

FIG. 2

This figure shows a cross-sectional view of a skin plate product according to the invention where holes in the matrix-forming material (10) extend from one surface to the other surface and are filled with a second material (11) on one side of the product and a different third material (12) on the other. Note that materials (11) and (12) are different but are considered as one zone. This one zone (the zones comprising the second material) extend trough the entire thickness of the product.

In this preferred embodiment, the surface areas constituted by the second material are different on the two faces of the product; that is, the surface area of the second material on one side of the product is zero. This feature is beneficial if the second material provides body fluid absorption capacity but little adhesion to skin. In this case it may be of value to reduce the area of the second material in contact with the skin but still have sufficient volume of the second material to ensure absorption capacity.

Similarly, the second material may have release properties (of a biologically active substance) but have low adhesion or absorption properties. Again it may be important to reduce the area of the second material in contact with the skin without reducing the volume of the second material.

Alternatively, if the second material has low cohesion but provides good adhesion, high absorption, efficient release of an active substance, or is particularly skin-friendly it may be useful to have a large area of the second material facing the skin without increasing the volume of the second material.

The product can be produced by firstly making holes in the matrix-forming material e.g. by using laser-drilling, thereafter applying the second material (11) onto the surface of the matrix-forming material (10) and rolling over the surface so that the second material will be displaced in to the holes. The amount of second material in the holes depends on the amount of second material applied to the surface of the matrix-forming material. The third material (12) can be applied in the same or similar manner as the second material (11).

FIG. 3

This figure shows a skin plate product comprising a matrix-forming material (1) intersected by a plurality of holes, where the holes contain a second material (2). The second material (2) does not fill the whole volume of the holes (1) leaving a pocket of air in the top of the holes. Thus, the skin plate product shown in this figure is not completely flat. This embodiment is particularly advantageous where the second material (2) is a swellable material. When swelling during use, this second material will gradually fill the left over space.

If the second material swells due to absorption of body fluids or water this has much less consequence for the first matrix-forming material, which in the prior art products must be able to follow the thickness increase of the second material.

FIG. 4

The invention claimed is:

1. A method for assembling an adhesive device having a first matrix-forming material with holes and a second material, the method comprising:
    (a) providing a first matrix-forming film;
    (b) designing a predetermined pattern of holes, where the holes are in known positions;
    (c) creating the predetermined pattern of holes in said film to form said matrix forming material;
    (d) composing the second material with a Tm lower than the Tm of the first material, while enabling an increase in the Tm of the second material;
    (e) assembling the adhesive device by filling the holes of the first matrix-forming material of step (b) with the second material of step (c) at a temperature where the second material is deformable and the first material is non-deformable; and
    (f) increasing the Tm of the second material.

2. The method according to claim 1, wherein step (f) is carried out by adding a melting point lowering substance to the second material.

3. The method according to claim 2, wherein the melting point lowering substance is a solvent.

4. The method according to claim 2, wherein step (f) further comprises evaporation of the melting point lowering substance.

5. The method according to claim 2, wherein the melting point lowering substance is a plasticiser.

6. The method according to claim 2, wherein step (f) is carried out by migration of the melting point lowering substance into the matrix-forming material.

7. The method according to claim 1, wherein step (f) is carried out by adding a two component reactive polymer system to the second material.

8. The method according to claim 7, wherein step (f) is carried out by inducing a reaction between the two component reactive polymer system.

9. The method according to claim 1, wherein step (f) is carried out using a two component reactive polymer system, the two component reactive polymer system having a first component and a second component, through migration of the second component from the first matrix-forming material to the second material, where the second material includes the second component of the reactive polymer system, followed by induction of a reaction between the two components of the two component reactive polymer system.

10. The method according to claim 1, wherein the Tm of the provided second material is 10° C. higher than the Tm of the matrix-forming material.

11. The method according to claim 1, wherein at least one of the first matrix-forming material and the second material is a skin friendly adhesive.

12. The method according to claim 11, wherein the first matrix-forming material is skin friendly.

13. The method according to claim 1, wherein the holes in the first matrix-forming material are created using a laser.

14. The method according to claim 1, wherein the second material is skin friendly.

15. A method for assembling an adhesive device having a first matrix-forming material with holes and a second material, the method comprising:
    (a) providing a first matrix-forming film;
    (b) creating holes in said film by punching machines, drills, pins, water jet technology, lasers, or combinations thereof to form said first matrix forming material;
    (c) composing the second material with a Tm lower than the Tm of the first material, while enabling an increase in the Tm of the second material;
    (d) assembling the adhesive device by filling the holes of the first matrix-forming material of step (b) with the second material of step (c) at a temperature where the second material is deformable and the first material is non-deformable; and
    (e) increasing the Tm of the second material.

16. The method according to claim 15, wherein step (e) is carried out by adding a melting point lowering substance to the second material.

17. The method according to claim 16, wherein the melting point lowering substance is a solvent.

18. The method according to claim 16, wherein step (e) further comprises evaporation of the melting point lowering substance.

19. The method according to claim 16, wherein the melting point lowering substance is a plasticiser.

* * * * *